US009039612B2

(12) United States Patent
Mielekamp et al.

(10) Patent No.: US 9,039,612 B2
(45) Date of Patent: May 26, 2015

(54) INTERACTIVE DETERMINATION OF COILING PARAMETERS

(75) Inventors: Pieter Maria Mielekamp, Eindhoven (NL); Drazenko Babic, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 302 days.

(21) Appl. No.: 13/500,693

(22) PCT Filed: Oct. 14, 2010

(86) PCT No.: PCT/IB2010/054647
§ 371 (c)(1),
(2), (4) Date: Apr. 6, 2012

(87) PCT Pub. No.: WO2011/048530
PCT Pub. Date: Apr. 28, 2011

(65) Prior Publication Data
US 2012/0203266 A1    Aug. 9, 2012

(30) Foreign Application Priority Data
Oct. 21, 2009   (EP) ..................................... 09173664

(51) Int. Cl.
A61B 5/00     (2006.01)
G06G 7/58     (2006.01)
A61B 17/12    (2006.01)
A61B 19/00    (2006.01)

(52) U.S. Cl.
CPC ....... *A61B 17/12022* (2013.01); *A61B 17/1214* (2013.01); *A61B 2019/463* (2013.01)

(58) Field of Classification Search
CPC ........... A61B 2560/00; A61B 2560/02; A61B 2560/0204; A61B 2560/0209; A61B 2560/0214; A61B 2560/0219; A61B 2560/0223; A61B 2560/0228; A61B 2560/0233; A61B 2560/0238
USPC ....................... 600/587, 595, 33, 300; 703/11
See application file for complete search history.

(56) References Cited

U.S. PATENT DOCUMENTS

| 5,825,908 | A | 10/1998 | Pieper et al. |
|---|---|---|---|
| 6,458,127 | B1 | 10/2002 | Truckai et al. |
| 2002/0165450 | A1 | 11/2002 | Sanchez et al. |
| 2007/0083226 | A1 | 4/2007 | Buiser et al. |
| 2007/0208277 | A1 | 9/2007 | Rioux et al. |
| 2008/0281181 | A1 | 11/2008 | Manzione et al. |
| 2009/0310840 | A1* | 12/2009 | Mohamed et al. ............ 382/131 |

FOREIGN PATENT DOCUMENTS

| WO | WO0229723 | 4/2002 |
|---|---|---|
| WO | 2009014528 A1 | 1/2009 |

OTHER PUBLICATIONS

Menno Sluzewski, MD, PhD, et al. "Relation between Aneurysm Volume, Packing, and Compaction in 145 Cerebral Aneurysms Treated with Coils", Jun. 2004, Radiology, vol. 231, Issue 3, 653-658.*
M. Piotin et al., "Intracranial Aneurysms: Treatment with Bare Platinum Coils-Aneurysm Packing, Complex Coils, and Angiographic Recurrence", Radiology: vol. 243: No. 2, May 2007.
Bruijns, "Local Distance Thresholds for Enhanced Aneurysm Labelling", Philips Research Laboratories, Eindhoven, The Netherlands, pp. 148-152.

* cited by examiner

*Primary Examiner* — Max Hindenburg
*Assistant Examiner* — Jonathan M Foreman

(57) ABSTRACT

A coiling parameterization tool includes a processor and a display for displaying values of lumen volume, packing and coiling parameters for filling a lumen in relation to a desired packing. The processor is configured to detect a change in one of the displayed values and, in response to the change, to automatically evaluate, change and display remaining values displayed on the display.

14 Claims, 2 Drawing Sheets

INTERACTIVE DETERMINATION OF COILING PARAMETERS

FIELD OF THE INVENTION

The invention relates to determining coiling parameters for filling a lumen with at least one coil.

BACKGROUND OF THE INVENTION

Michel Piotin et al., Intracranial Aneurysms: Treatment with Bare Platinum Coils—Aneurysm Packing, Complex Coils, and Angiographic Recurrence, Radiology: Volume 243: Number 2—May 2007, pp. 500-508 describe an assessment, with three-dimensional rotational angiography, of the relationship between packing, helical and complex coils, and angiographic recurrence of aneurysms treated with coils. Such treatments are performed by endovascular deployment of one or several coils in an aneurysm.

An aneurysm is one example for a lumen to be filled with coils.

In the article by M. Piotin et al., packing is defined as the ratio of coil volume to aneurysm volume.

SUMMARY OF THE INVENTION

In the article by M. Piotin et al. the aneurysms which were treated were small, with a mean aneurysm volume of 152 mm³. For such aneurysms it was found that packing does not play an important role in the recurrence rate, whereas previous studies indicated that packing of more than 20% to 25% was found to protect against recurrence. For treatment of said small aneurysms packing of 27% for complex coils and 26% for helical coils was employed. The choice of the type (helical or complex) and brand of coil used was up to the physician performing the treatment procedure.

An object of the invention is providing a tool for easily and appropriately determining coiling parameters for filling a lumen with at least one coil.

The invention provides a method including the steps of determining the volume of a lumen to be filled by at least one coil, and interactively determining at least one coil parameter in relation to the required packing. The interactive determination of coiling parameters provides a wide choice of selections for a practitioner using the method according to the invention, prior to or during deployment of coils.

The volume of the lumen may be preset, or may be obtained based on three-dimensional rotational angiography, as suggested by J. Bruijns, Fully-Automatic Labelling of Aneurysm Voxels for Volume Estimation, Procs BVM, 2003, pp. 51-55.

According to an embodiment of the invention, the at least one coil parameter is a number of coils, a coil thickness, or a coil length. The packing may be predetermined, and the number of coils may be determined based on the packing and at least one further coil parameter. Alternatively, the number of coils based on at least one further coil parameter may be predetermined, and the packing may be determined based thereon.

According to an embodiment of the method of the invention, the at least one coil parameter includes a first coil parameter set and at least a second coil parameter set. Each one of these coil parameter sets relates to a certain type of coil. A first number of coils of a first type based on the first coil parameter set may be determined, and a second number of coils of a second type based on the second coil parameter set may be determined. Therefore, for interactively determining coiling parameters different coil types might be used for filling the same lumen, in consideration of a desired packing, of a particular shape of the lumen, and so on. Of course, the number of types of coils is not limited to two, such that, for example, also three or more different types of coils might be used.

According to another embodiment of the inventive method, the values of the entities (or at least some entities) used in the method are displayed on the screen of a display device. This allows an easy interaction with and information of an operator.

The invention also relates to a device with an input unit configured to enter at least one selected entity used in the method, a processor configured to interactively determine said at least one coil parameter, and an output unit configured to output at least one selected entity used in the method. Such a device enables an easy interaction with an operator who, after having entered a selected entity (for example coil parameter), will be immediately informed of a corresponding output.

The invention also provides a computer program product enabling a processor to carry out the method according to the invention or any embodiment thereof.

DETAILED DESCRIPTION OF EMBODIMENTS

Figure 1:
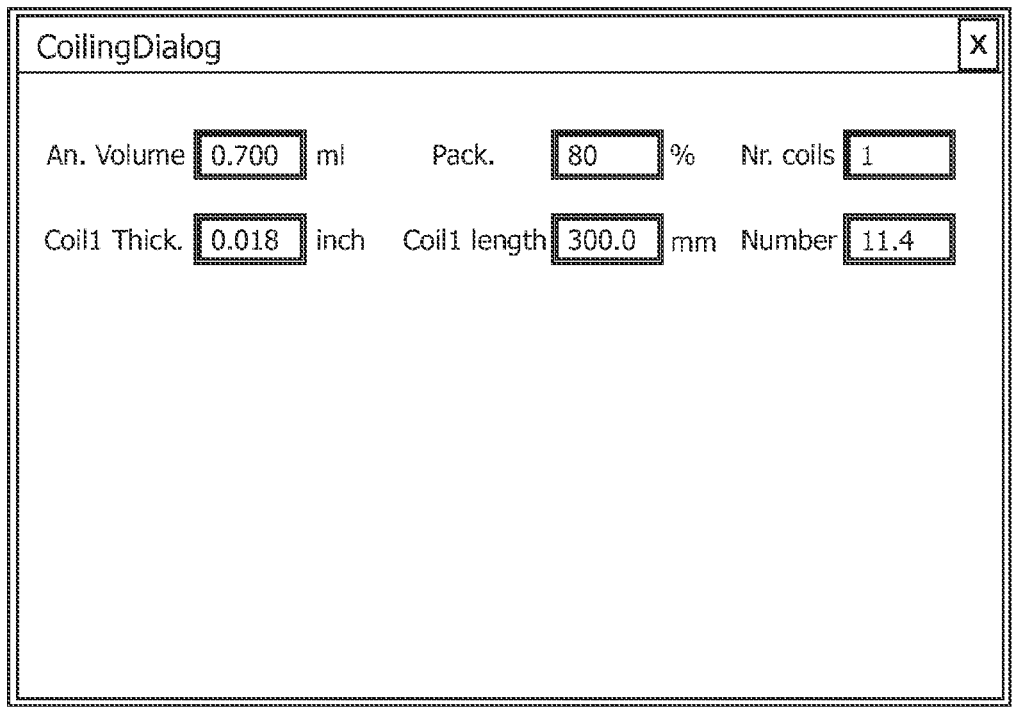
FIGS. 1(A) to 1(D) show screenshots of a screen of a display unit (output unit) with entities or parameters entered by a user or provided by a device according to the invention.
Figure 1:
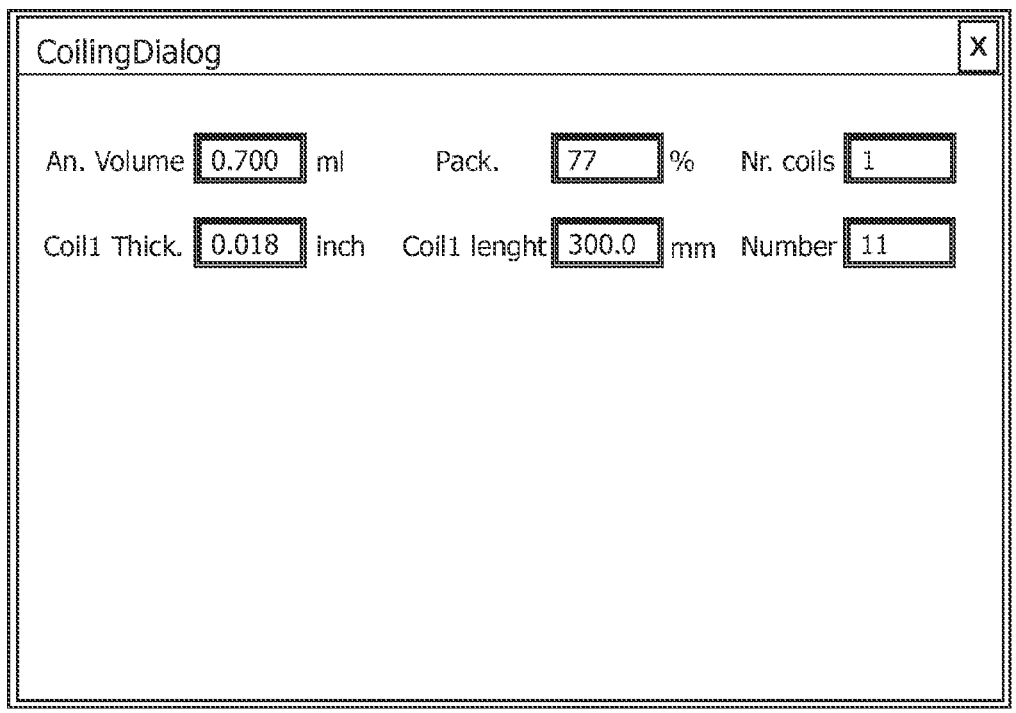
Figure 1:
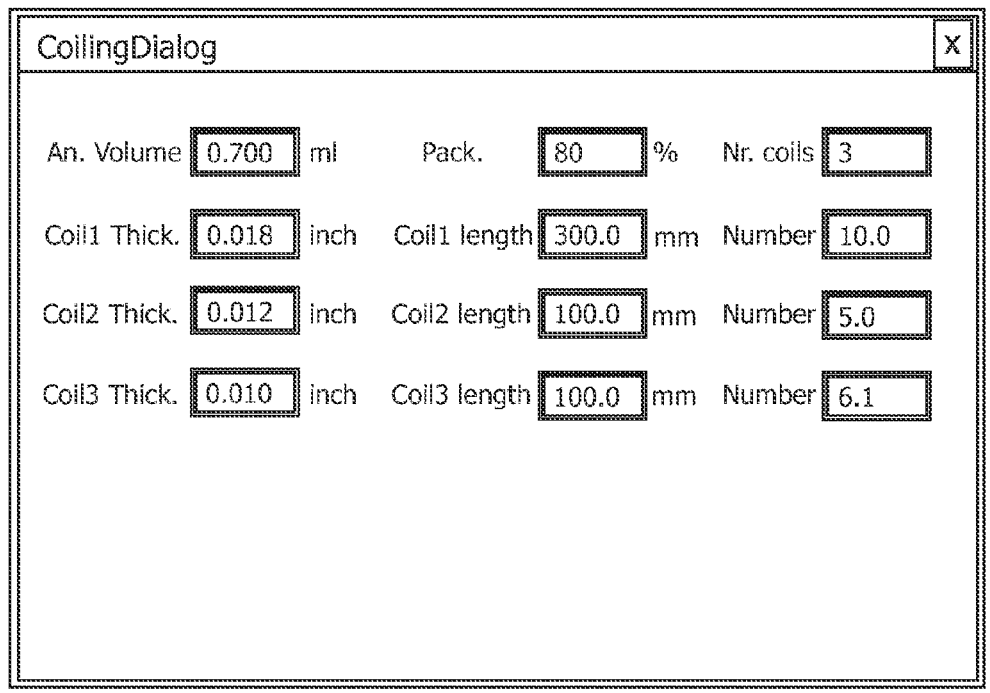
Figure 1:
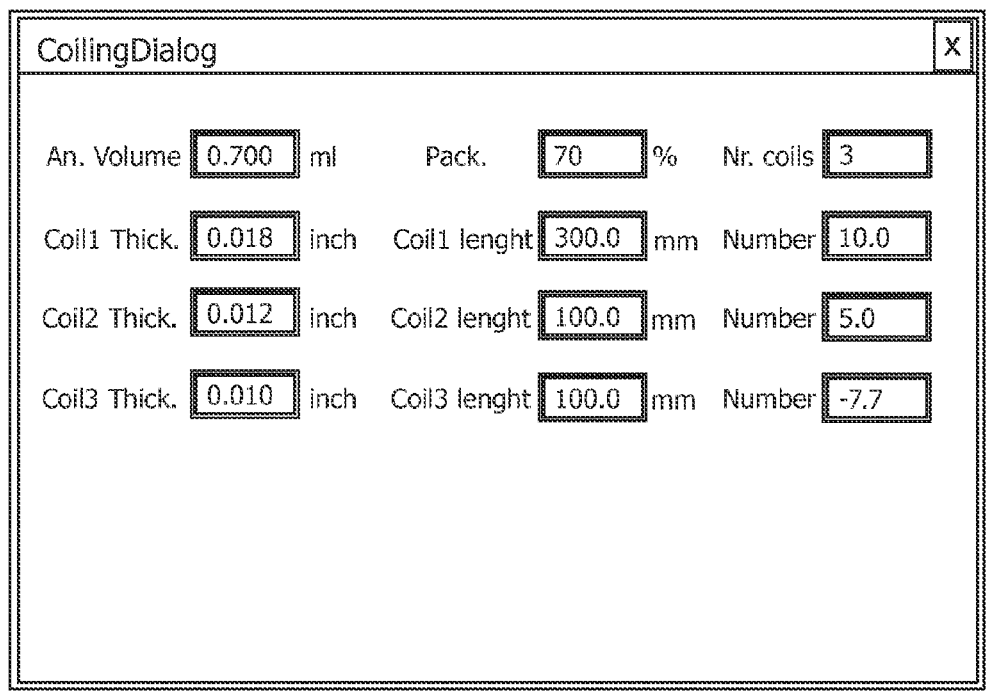

The invention will be described in more detail hereinafter based on preferred or advantageous embodiments thereof.

The following terms and definitions will be used.

aneurysm volume AV in ml (1 ml=1000 mm³)

coil thickness WD: thickness (in inches, 1 in=25.4 mm); i.e. thickness of the coil wire coil length WL: length (in mm) of the coil wire coil volume $VC=(\pi/4) \times WD^2 \times WL$ (in case of a cylindrical coil wire with a thickness WD)

packing=VC/AV (dimensionless parameter)

number of coils=(packing) AV/VC

The following procedure explains the method of the invention. Indicated in (row/column) below are user input (in bold) and system response (in italics). Such matrizes may be presented as screenshots, for example. Step 1 starts with an aneurysm volume AV of 0.168 ml, a packing of 80%, a single type (1) of a coil, a coil thickness of 0.016 inches, and a coil length WL of 200 mm. This results in that a number of 5.2 such coils are required.

Since the coil volume VC is determined based on the volume of the coil wire, i.e. on the volume of the material of the coil the value of VC is independent of the particular shape of the coil.

In more detail, indicated hereinafter in (row/column) are:

(1,1) aneurysm volume AV in ml
(1,2) packing in %
(1,3) number of coil types
(2,1) coil thickness WD in inches
(2,2) coil length WL in mm
(2,3) number of coils (of the type in row 3)
Step 1 At start-up this dialog comes up

| 0.168 | 80  | 1   |
|-------|-----|-----|
| 0.016 | 200 | 5.2 |

Step 2 Changing the number of different coils (1→2) adds the third row

| 0.168 | 80  | 2   |
| ----- | --- | --- |
| 0.016 | 200 | 5.2 |
| 0.014 | 100 | 0   |

Step 3 Changing the number of coils to 3 changes the packing density to 46

| 0.168 | 46  | 2 |
| ----- | --- | - |
| 0.016 | 200 | 3 |
| 0.014 | 100 | 0 |

Step 4 Changing the packing modifies the number of coils of the last row

| 0.168 | 80  | 2   |
| ----- | --- | --- |
| 0.016 | 200 | 3   |
| 0.014 | 100 | 5.7 |

Step 5 Changing the coil thickness changes the packing

| 0.168 | 71  | 2   |
| ----- | --- | --- |
| 0.016 | 200 | 3   |
| 0.012 | 100 | 5.7 |

Step 6 Changing the packing modifies the number of coils of the last row

| 0.168 | 80  | 2   |
| ----- | --- | --- |
| 0.016 | 200 | 3   |
| 0.012 | 200 | 7.8 |

This can be repeated with additional rows. In general, modifying coil parameters or aneurysm volume will change packing. Changing packing will change number of coils in the last row.

There are a few configurable defaults as follows:
1) The metrics
2) Size and length of the coils;

Coils are added automatically with size 0 and thickness, length as shown below.

| 0.016 | 200 |
| ----- | --- |
| 0.014 | 100 |
| 0.012 | 100 |
| 0.010 | 100 |

The selection is based on the last coil thickness.

| 0.168 | 80  | 4   | Changing number of different coils to 4 at state 4 |
| 0.016 | 200 | 3   | will add sizes 0.012 and 0.010 (i.e. thickness)    |
| 0.014 | 100 | 5.7 |                                                    |
| 0.012 | 100 | 0   |                                                    |
| 0.010 | 100 | 0   |                                                    |
| 0.168 | 80  | 3   | Changing number of different coils to 3 at state 6 |
| 0.016 | 200 | 3   | will add size 0.010                                |
| 0.012 | 100 | 7.8 |                                                    |
| 0.010 | 100 | 0   |                                                    |

FIGS. 1(A) to 1(C) show screens (screenshots) of a display device (output unit) of a device according to the invention, in various stages of the method according to the invention.

In FIG. 1(A) the number of coils is 11.4, for the coil parameters indicated in the figure and a packing of 80%. If the packing is changed to 77%, the number of coils is 11 as shown in FIG. 1(B).

FIG. 1(C) shows a case where three (Nr. coils) different coils are used, with coil parameters indicated in rows 2 to 4 in the figure, and a packing of 80%. If then the packing is reduced to 70% as shown in FIG. 1(D), the negative number −7.7 for the number of coils indicates that 7.7 coils of the third coil type in the fourth row will have to be removed.

In summary, the invention provides an easy to use coiling parameterization tool that allows a user to interactively evaluate coiling parameters for filling a lumen in relation to a desired packing and the automatically determined or manually indicated volume of the lumen.

The lumen may be an aneurysm to be filled with at least one coil through a medical intervention, for providing an embolization.

Other fields of filling a lumen with coils are vessels to be filled with coils which act as a catalyst or contain a catalyst.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein certain entities do not have to be entered by a user, but are presented as a list of default values for selection by the user, e.g. a list of coil parameters of coils which are commercially available and/or comply with regulations (in particular in the medical field).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solidstate medium supplied together with or as part of other hardware, but may also be distributed I other forms, such as via the Internet or other wired or wireless telecommunication systems.

The invention claimed is:

1. A method of interactively determining coiling parameters for filling a lumen with at least one coil, comprising acts of:
   determining a lumen volume of the lumen;
   interactively determining at least one coil parameter of the coiling parameters in relation to a packing based on the determined lumen volume of the lumen, wherein the packing is a ratio of a coil volume of the at least one coil to the lumen volume of the lumen;
   displaying on a screen of a display device values of the lumen volume, the packing, a number of coil sets, and the least one coil parameter, the least one coil parameter including coil thicknesses of the each coil, coils lengths of the each coil and a number of coils in each of the coil sets;

changing a value of one of the values displayed on the screen; and in response to the changing act, automatically changing at least one of remaining values displayed on the screen.

2. The method of claim 1, wherein the at least one coil parameter is at least one of a number of coils, a coil thickness, and a coil length.

3. The method of claim 2, wherein the packing is predetermined, and the number of coils is determined based on the packing and at least one further coil parameter.

4. The method of claim 2, wherein the number of coils based on at least one further coil parameter is predetermined, and the method further comprises determining the packing based on the predetermined number of coils.

5. The method of claim 1, wherein the at least one coil parameter includes a first coil parameter set and at least a second coil parameter set.

6. The method of claim 5, further comprising acts of
determining a first number of coils of a first type based on the first coil parameter set; and
determining a second number of coils of a second type based on the second coil parameter set.

7. The method of claim 1, wherein the interactively determining act comprises acts of:
displaying the lumen volume, a packing value of the packing, a number of coil sets, and for each coil in a coil set of the coil sets, displaying a coil thickness, a coil length and a number of coils;
changing the number of coil sets to a changed coil sets number;
in response to the changing act, displaying a further coil set and changing the packing to a changed packing value;
changing the changed packing value back to the packing value;
in response to the act of changing the changed packing, changing a value of the number of coils of the further coil set;
in response to the act of changing the value of the number of coils, changing the packing value to a further changed packing value;
changing the further changed packing value back to the packing value; and
in response to the act of changing the further changed packing value, changing the value of the number of coils of the further coil set to a further value of the number of coils of the further coil set.

8. A device for interactively determining at least one coiling parameter of at least one coil used for filling a lumen, the device comprising:
an input unit configured to receive input values of a lumen volume of the lumen and a packing, wherein the packing is a ratio of a coil volume of the of least one coil to the lumen volume;
a processor configured to interactively determine said at least one coil parameter based on the input values; and
an output unit configured to output values of the lumen volume, the at least one coil parameter and the packing, wherein the output unit comprises a display and wherein, in response to a change in a value of one of the values displayed on the display, the processor is further configured in automatically change at least one of remaining values displayed on the display.

9. The device of claim 8, wherein the at least one coil parameter is at least one of a number of coils, a coil thickness, and a coil length of the of least one coil.

10. The device of claim 9, wherein the packing is predetermined, and the number of coils is determined based on the packing and at least one further coil parameter of the at least one coil parameter.

11. The device of claim 9, wherein the number of coils is predetermined, and the packing is determined based on the predetermined number of coils and at least one further coil parameter.

12. The device of claim 8, wherein the output unit is further configured to display on the display a further value of a set number of coil sets, and wherein the values of the least one coil parameter displayed on the display includes a number of coils in each coil of the coils sets, coil thicknesses of the each coil, and coils lengths of the each coil, and
wherein the processor is further configured to change a value of one of the values and the further value displayed on the screen to a changed value and, in response to the changed value to automatically change at least one of remaining values displayed on the display.

13. The device of claim 8, wherein the processor is configured to interactively perform act of:
displaying the lumen volume, a packing value of the packing, a number of coil sets, and for each coil in a coil set of the coil sets, displaying a coil thickness, a coil length and a number of coils;
changing the number of coil sets to changed coil sets number;
in response to the changing act, displaying a further coil set and changing the packing to a changed packing value;
changing the changed packing value back to the packing value;
in response to the act of changing the changed packing, changing a value of the number of cons of the further coil set;
in response to the act of changing the value of the number of coils, changing the packing value to a further changed packing value;
changing the further changed packing value back to the packing value; and
in response to the act of changing the further changed packing value, changing the value of the number of coils of the further coil set to a further value of the number of coils of the further coil set.

14. A non-transitory computer readable medium comprising computer instructions which, when executed by a processor, configure the processor to interactively determine coiling parameters for filling a lumen with at least one coil by performing acts of:
determining a lumen volume of the lumen;
interactively determining at least one coil parameter of the coiling parameters in relation to a packing based on the determined lumen volume, wherein the packing is a ratio of a coil volume of the at least one coil to the lumen volume;
displaying on a screen of a display device values of the lumen volume, the packing, a number of coil sets, and the least one coil parameter, the least one coil parameter including coil thicknesses of the each coil, coils lengths of the each coil and a number of coils in each of the coil sets;
changing a value of one of the values displayed on the screen; and
in response to the changing act, automatically changing at least one of remaining values displayed on the screen.

\* \* \* \* \*